US008350126B2

(12) United States Patent
Kausch et al.

(10) Patent No.: US 8,350,126 B2
(45) Date of Patent: Jan. 8, 2013

(54) GREEN GARLIC AND METHODS OF PRODUCTION

(75) Inventors: Albert P. Kausch, Stonington, CT (US); Peter Sellew, Carlisle, MA (US)

(73) Assignee: Ophios, LLC, West Kingston, RI (US)

( * ) Notice: Subject to any disclaimer, the term of this patent is extended or adjusted under 35 U.S.C. 154(b) by 0 days.

(21) Appl. No.: 13/066,214

(22) Filed: Apr. 8, 2011

(65) Prior Publication Data

US 2011/0196034 A1   Aug. 11, 2011

Related U.S. Application Data

(62) Division of application No. 11/579,295, filed as application No. PCT/US2005/015584 on May 4, 2005, now Pat. No. 7,937,889.

(60) Provisional application No. 60/568,354, filed on May 5, 2004.

(51) Int. Cl.
*A01H 5/00*   (2006.01)

(52) U.S. Cl. ........................................ 800/298

(58) Field of Classification Search ............... 47/58.1 R, 47/58.1 FV; 800/200, 298, 295
See application file for complete search history.

(56) References Cited

U.S. PATENT DOCUMENTS

| 5,725,895 A | 3/1998 | Fahey et al. |
| 5,913,729 A * | 6/1999 | Kajimura .................. 47/58.1 R |
| 5,968,505 A | 10/1999 | Fahey et al. |
| 5,968,567 A | 10/1999 | Fahey et al. |
| 6,308,456 B1 | 10/2001 | Barten |
| PP12,761 P2 | 7/2002 | de Groot |

FOREIGN PATENT DOCUMENTS

WO   WO 99/21008 A1   4/1999

OTHER PUBLICATIONS http://www.wisegeek.com/what-is-green-garlic.htm; pp. 1-6; 2012.*
Garlic from Snakeroot Organic Farm, http://home.gwi.net/~troberts/farm/Garlic.html, Apr. 20, 2005.
Banerjee et al., "The Interactions of Allium Sativum Leaf Agglutinin with a Chaperonin Group of Unique Receptor Protein Isolated from a Bacterial Endosymbiont of the Mustard Aphid," *J. Biol. Chem.* 279:23782-23789 (2004).
Bodner et al., "Garlic Production," Fact Sheet, Ministry of Agriculture and Food, http://www.gov.on.ca/OMAFRA/english/crops/facts/97-007.htm, Apr. 20, 2005.
Boscher et al., "Qualitative and Quantitative Comparison of Volatile Sulphides and Flavour Precursors in Different Organs of Some Wild and Cultivated Garlics," *Biochem. Sys. Ecol.* 23:787-791 (1995).
Briggs et al., "Administration of Raw Onion Inhibits Platelet-Mediated Thrombosis in Dogs," *J. Nutr.* 131:2619-2622 (2001).
Briggs et al., "Variation in Economically and Ecologically Important Traits in Onion Plant Organs During Reproductive Development," *Plant Cell Environ.* 25:1031-1037 (2002).

(Continued)

*Primary Examiner* — Kent L Bell
(74) *Attorney, Agent, or Firm* — Klarquist Sparkman, LLP

(57) ABSTRACT

A new vegetable, referred to herein as green garlic, grown from garlic bulbils is disclosed. In particular examples, the green garlic is rich in one or more thiosulfinates. Methods of producing green garlic are also disclosed. In some examples, such methods permit year-round commercial production of green garlic.

27 Claims, 1 Drawing Sheet
(1 of 1 Drawing Sheet(s) Filed in Color)

OTHER PUBLICATIONS

Coley-Smith, "Interactions between *Sclerotium cepivorum* and Cultivars of Onion, Leek, Garlic and *Allium fistulosum*," *Plant Pathol.* 35:362-369 (1986).

Croci et al., "Effect of Gamma Rays on Seed Cloves of Garlic (*Allium sativum* L.) at Post-Harvest: Reversion by Exogenous Growth Regulators," *Environ. Exper. Bot.* 27:1-5 (1987).

Etoh et al., "Diversity, Fertility and Seed Production of Garlic," *Allium Crop Science: Recent Advances*, pp. 101-117 (2002).

Gori, "Ultrastructural Changes in the Wall of the Sporogenous Cells in *Allium sativum*, Clone Piemonte During Microsporogeneis," *Ann. Bot.* 51:139-143 (1983).

Heldman, "Identifying Food Science & Technology Research Needs. An IFT Task Force Identifies Research Needed to Delvier Safe and Health-Enhancing Foods that Improve the Quality of Life of Consumers," *Food Technol.* 58:32-40 (2004).

Hughes et al., "Synthesis of the Flavour Precursor, Alliin, in Garlic Tissue Cultures," *Phytochem.* 66:187-194 (2005).

Ipek et al., "Comparison of AFLPs, RAPD Markers, and Isozymes for Diversity Assessment of Garlic and Detection of Putative Duplicates in Germplasm Collections," *J. Amer. Soc. Hort. Sci.* 128:246-252 (2003).

Ipek et al., "Demonstration of Linkage and Development of the First Low-Density Genetic Map of Garlic, Based on AFLP Markers," *Theor. Appl. Genet.* 110:228-236 (2005).

Kim et al., "Enhanced Shoot and Bulblet Proliferation of Garlic (*Allium sativum* L.) in Bioreactor Systems," *J. Horticult. Sci. Biotechnol.* 79:818-822 (2004).

Kubec et al., "Isolation of *S-n*-Butylcysteine Sulfoxide and Six *n*-Butyl-Containing Thiosulfinates from *Allium siculum*," *J. Nat. Prod.* 65:960-964 (2002).

Kubec et al., "*Allium* Discoloration: Precursors Involved in Onion Pinking and Garlic Greening," *J. Agric. Food Chem.* 52:5089-5094 (2004).

Leys et al., "The Response of Wild Garlic (*Allium vineale*) to the Timing of Spray Applications of Chlorsulfuron," *Weed Sci.* 34:718-723 (1986).

Leys et al., "Comparison of Chlorsulfuron and Metsulfuron for Control of *Allium vineale* L.," *Weed Res.* 27:35-41 (1987).

Loidl, "Synaptonemal Complex Spreading in *Allium*. II. Tetraploid *A. vineale*," *Can. J. Genet. Cytol.* 28:754-761 (1986).

Malik et al., "The 26S Proteasome in Garlic (*Allium sativum*): Purification and Partial Characterization," *J. Agric. Food Chem.* 52:3350-3355 (2004).

Manabe et al., "Alliinase [*S*-alk(en)yl-L-Cysteine Sulfoxide Lyase] from *Allium tuberosum* (Chinese Chive)—Purification, Localization, cDNA Cloning and Heterologous Functional Expression," *Eur. J. Biochem.* 257:21-30 (1998).

McGregor, "Taste Modification in the Biotech Era—Advances in Understandng the Science of Taste are Allowing a Biotechnological Approach to the Identification and Development of Novel Taste Modifiers such as Bitter Blockers and Sweetness Potentiators," *Food Technol.* 58:24-30 (2004).

Mondy et al., "Aroma Analysis of Fresh and Preserved Onions and Leek by Dual Solid-Phase Microextraction-Liquid Extraction and Gas Chromatography-Mass Spectrometry," *J. Chromatogr A* 963:89-93 (2002).

Motsei et al., "Screening of Traditionally Used South African Plants for Antifungal Activity Against *Candida albicans*," *J. Ethnopharmacol.* 86:235-241 (2003).

Muoio et al., "A Comparative Study of Sulphur Content of Some *Allium L.* Species," *Economic Botany* 58:227-230 (2004).

Myers et al., "Continuous Callus Production and Regeneration of Garlic (*Allium sativum* L.) Using Root Segments from Shoot Tip-Derived Plantlets," *Plant Cell Reports* 17:726-730 (1998).

Nishimura et al., "Thermochemical Transformation of Sulfur Compounds in Japanese Domestic *Allium, Allium victorialis* L.," *Biofactors* 13:257-263 (2000).

Nishimura et al., "Antioxidative Activity of Sulfur-Containing Compounds in *Allium* Species for Human LDL Oxidation in Vitro," *Biofactors* 21:277-280 (2004).

Pooler et al., "Characterization and Classification of Isozyme and Morphological Variation in a Diverse Collection of Garlic Clones," *Euphytica* 68:121-130 (1993).

Shimon, Alliin Lyase (Alliinase) from Garlic (*Allium sativum*): Crystallization and Preliminary X-Ray Characterization, *Acta Cryst.* D58:1335-1337 (2002).

Simon, "Genetic Analysis of Pungency and Soluble Solids in Long-Storage Onions," *Euphytica* 82:1-8 (1995).

Simon et al., "Flowering, Seed Production, and the Genesis of Garlic Breeding," *Plant Breeding Rev.* 23:211-244 (2003).

Tabor et al., "Influence of Storage Duration on Field Sprouting, Maturity and Yield of Some Garlic (*Allium sativum* L.) Cultivars at Debre Zeit, Ethiopia," *J. Hort. Sci. Biotechnol.* 79:871-876 (2004).

Van Damme et al., "Isolation and Characterization of Alliinase cDNA Clones from Garlic (*Allium sativum* L.) and Related Species," *Eur. J. Biochem.* 209:751-757 (1992).

Volk et al., "Genetic Diversity Among U.S. Garlic Clones as Detected Using AFLP Methods," *J. Amer. Soc. Hort. Sci.* 129:559-569 (2004).

Volk et al. "Low-Temperature Storage of Garlic for Spring Planting," *HortScience* 39:571-573 (2004).

Wei et al., "Changes in Growth and Gene Expression Induced by Sulfur Deficiency in Garlic," *J. Plant Nutr.* 25:2817-2829 (2002).

\* cited by examiner

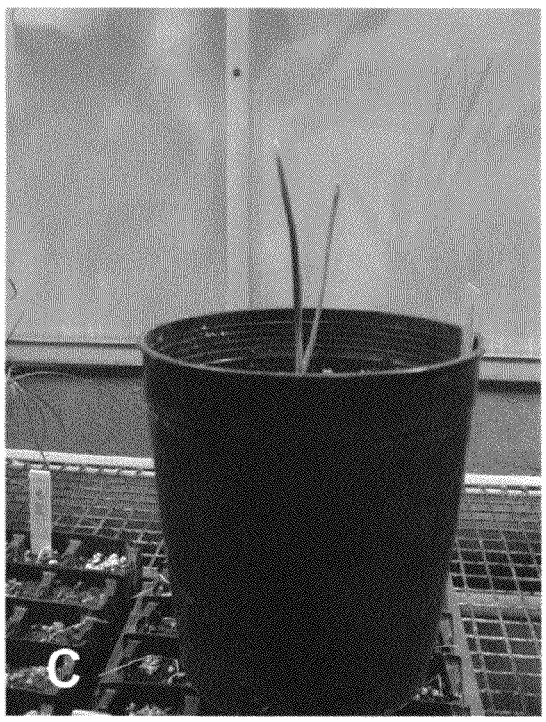

GREEN GARLIC AND METHODS OF PRODUCTION

CROSS REFERENCE TO RELATED APPLICATIONS

This application is a divisional of U.S. application Ser. No. 11/579,295, filed Nov. 1, 2006, now U.S. Pat. No. 7,937,889, which is the U.S. National Stage of International Application No. PCT/US2005/015584, filed May 4, 2005, which was published in English under PCT Article 21(2), which in turn claims the benefit of U.S. Provisional Application No. 60/568,354, filed May 5, 2004. All applications are incorporated herein in their entirety.

FIELD

This application relates to green garlic which in particular examples includes therapeutic amounts of one or more thiosulfinates, and methods of producing such green garlic. Methods of increasing the therapeutic amount of one or more thiosulfinates in a mammal, by administering the green garlic to the mammal, are also provided.

BACKGROUND

Garlic is one of the oldest horticultural crops. Worldwide production of garlic is nearly 10 million tonnes on nearly a million hectares. Because garlic seedlings grown from true seeds lack vigor and plants in these early generations can manifest unfavorable growth characteristics (such as deformed leaves, stunted roots, and limited bulb production), garlic production relies upon asexual propagation of the crop. The growth of a garlic plant typically begins from an individual clove that has been exposed to cool temperatures (15° C. or less) and depleted or "broken" dormancy (Rahim and Fordham, *Scientia Hort.* 37:25-38, 1988; Takagi, H. 1990. Garlic *Allium sativum* L. p. 109-146. In: J. L. Brewster and H. D. Rabinowitch (ads.), Onions and allied crops, v. III. biochemistry. food science, and minor crops. CRC Press. Boca Raton, Fla.). The root system and flat leaves usually develop before clove initiation (bulbing) ensues from inner (younger) leaf axillary buds. Plant maturation and senescence usually ensues after garlic bulb production. As the main stem of the bulb die, intact and living basal plates remain on each clove to carry on future growth.

The major distinction among garlic clones is the tendency to produce a flower stalk, or not. Those producing a flower stalk are referred to as "bolting," "stalking," or "hard neck" types, whereas those without a flower stalk are "non-bolting," "non-stalking," or "soft neck." Sometimes a third category, "incomplete or partial bolting," is used for clones in which the inflorescence begins to develop but stem elongation is incomplete and mature flowers do not develop.

Development of the floral apical meristem in bolting garlic requires exposure to low temperatures (such as less than 5° C.) before onset of the primary growth period. Complete bolting in garlic involves floral induction, scape elongation, inflorescence development, and floral maturation. During scape elongation, the meristematic region at its tip begins to differentiate floral initials and subdivides into identifiable flowers interspersed with bulbils. Because development of the garlic seed stalk precludes further vegetative growth, garlic farmers remove and discard the scapes to promote growth of the garlic cloves.

Current methods of garlic bulb production include planting a clove of or from a mature garlic bulb in the fall (in the Northern Hemisphere). In the spring or early summer, fresh garlic shoots appear from the cloves.

Garlic and extracts thereof have been indicated to have positive effects on circulation and pulmonary function, as well as potential anti-cancer affects (for example see WO 99/21008). Most of the active ingredients in crushed garlic are sulfur-containing compounds. Allicin (thio-2-propene-1-sulfinic acid S-allyl ester) is the primary component that is understood to produce many of the medicinal benefits attributed to garlic. The intact garlic clove does not contain allicin, but rather contains its precursor alliin (S-allyl-L-cysteine sulfoxide). Allicin is formed by crushing garlic, which allows the enzymatic conversion by alliinase (C-S-lyase, also known as alliin lyase [E.C. 4.4.1.4]) of alliin to allicin, as well as pyruvate, and ammonia. Alliin and alliinase are found in different compartments of the garlic cloves. When garlic is cut or crushed, the membranes of these compartments are broken so that the enzyme can react with alliin.

Although many health benefits of garlic have been observed, such benefits are reduced by cooking garlic, since the therapeutic compounds in garlic are adversely affected by heat. Unfortunately, most individuals do not prefer to eat significant quantities of raw garlic cloves. Furthermore, processes which dry garlic to make it into a powder or pill also change the composition and concentration of the sulfur-containing compounds. Therefore, the ability to provide these therapeutic compounds in a fresh vegetable which can easily be consumed raw (uncooked) is desirable.

SUMMARY

The inventors have developed a new vegetable, referred to herein as "green garlic", comparable in appearance to other members of the onion family such as green onions, scallions, and leeks, except that green garlic has a mild garlic flavor. Green garlic is produced from garlic bulbils obtained from hardneck garlic varieties. Current methods of hardneck garlic production include discarding the scapes that produce bulbils. This decapitation stimulates the clove formation for traditional garlic crops. Therefore, the methods disclosed herein for producing green garlic provide a use for discarded bulbils.

In particular examples, the green garlic plants of the present disclosure are similar in appearance to their onion relatives: a whitish bulb is present at the base of the plant instead of the familiar garlic cloves of a mature plant. Green garlic can be provided as a small, medium or large plant product, depending on the size of the bulbil used. For example, large bulbils, such as those that at least 9 mm in length, produce a leek-like green garlic (FIGS. 1A and 1C). Medium-sized bulbils, such as those that are 3.5-8.9 mm in length, produce a scallion-like green garlic (FIG. 1B). Small bulbils, such as those that are less than 3.5 mm in length, produce sprout-like green garlic (FIG. 1D). The green garlic products can be used as food products in a manner similar to their onion counterparts. The inventors have observed that the disclosed green garlic has a mild garlic flavor, thereby permitting consumption of the green garlic without cooking it.

Methods are provided for producing green garlic from hardneck garlic bulbils. Hardneck garlic varieties are known, and include, but are not limited to, the 'ophioscorodon' variety of *Allium sativum* L., as well as subvarieties thereof. In particular examples the method includes growing a hardneck garlic bulbil and subsequently harvesting the green garlic. In particular examples, the bulbils are incubated under conditions that break bulbil dormancy prior to growing the bulbil. Bulbils can be grown outdoors or indoors, for example in a greenhouse. Ideally, if bulbils are grown outdoors, they are grown in an area that permits more than seasonal production of green garlic, such as year-round production. The appropriate growing conditions can vary depending on the hardneck garlic variety used. However, such conditions can be determined using routine methods known by those skilled in the art (as well as methods disclosed herein). The disclosed methods can be used to produce commercial amounts of green garlic and provide a year-round supply of green garlic. In particular examples, commercial production of green garlic is at least 100 pounds of green garlic annually. Crops that include the planted bulbils, or the green garlic plants, are also disclosed herein.

Methods are also provided for producing a food product that includes one or more sulfur-containing compounds, such as one or more thiosulfinates. In particular examples, the method includes germinating a bulbil and harvesting the green garlic, thereby generating a food product that includes one or more sulfur-containing compounds. Exemplary sulfur-containing compounds include, but are not limited to: thio-2-propene-1-sulfinic acid S-allyl ester (allicin) S-allyl cysteine sulphoxide (alliin), S-methyl cysteine sulphoxide (methiin), trans S-1-propenyl cysteine sulphoxide (isoalliin), S-propyl cysteine sulphoxide (propiin), or combinations thereof.

Green garlic produced by the disclosed methods is also provided. In particular examples, green garlic desirably includes at least 0.5 milligrams (mg) of allicin per gram of green garlic as measured after 30-45 days of growth, such as 0.5-4 mg allicin/g green garlic. In some examples, the green garlic of *Allium sativum* var. 'ophioscorodon' subvariety Music (Accession number PI 515972; Accession numbers referred to herein correspond to those at USDA, ARS, WRPIS, Washington State University) includes at least 0.5 mg of allicin per gram of green garlic, at least 0.1 mg S-methyl cysteine sulphoxide (methiin; AllS(O)SMe) per gram of green garlic, at least 0.1 mg trans S-1-propenyl cysteine sulphoxide (isoalliin) per gram of green garlic, at least 0.1 mg S-propyl cysteine sulphoxide (propiin: AllS(O)SPropenyl) per gram of green garlic, or combinations thereof, at 30-45 days following planting, for example as measured by HPLC. Also provided are food products that include the green garlic, such as entrees, salads, and soups.

Methods are disclosed for increasing an amount of one or more sulfur-containing compounds, such as one or more thiosulfinates in a mammal, such as a human. Such methods can be used to treat (such as prevent) chronic pulmonary disease, or a vascular disease, for example by lowering blood pressure, decreasing ischemic injury, reducing serum cholesterol, reducing platelet aggregation, reducing amounts of plasma homocysteine, enhancing thrombolysis, or combinations thereof, in the mammal. In another example, such methods can be used to provide a chemoprotective effect to the mammal. In some examples, the method includes administering the disclosed green garlic (or a non-toxic extract thereof) to the mammal, thereby increasing the amount of thiosulfinates in the mammal. In some examples, the green garlic is not cooked prior to administration to the mammal, for example not exposed to a temperature that would substantially reduce the presence of thiosulfinates, such as allicin, in the green garlic. In a particular example, the green garlic is not exposed to at least 170° F. for more than 3 minutes. In particular examples, administration includes feeding raw green garlic of the present disclosure to the mammal, for example to protect coronary vascular function and lessen the severity of right heart hypertrophy in the mammal.

Also provided by the present disclosure is packaged or containerized green garlic. The packaging or container in which the green garlic is present in particular examples is one suitable for shipping of the green garlic or one suitable for sale of the green garlic. In some examples, the container is a pot which includes a growth media and the live green garlic. The green garlic in the container can be of any size suitable for shipping or sale. In particular examples, the green garlic in the container or package is of substantially a uniform size, such as a diameter of within 1 to 5 mm of each other.

The foregoing and other objects, features, and advantages of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-D are digital images showing four different green garlic plants produced from different sized bulbils. Bulbil size was measured as mean dry weight (g) per bulbil and mean size (mm) in the longest dimension. (A) *Allium sativum* var. 'ophioscorodon' subvariety Blanco De Huelma Zamora (Accession number PI 615423). Bulbils were 0.52±0.13 g and 14±5.4 mm in length. (B) *Allium sativum* var. 'ophioscorodon' subvariety Music (Accession number PI 515972). Bulbils were 0.05±0.033 g and 6±2.4 mm in length; (C) *Allium sativum* var. 'ophioscorodon' subvariety German Red (Accession number PI 540538). Bulbils were 0.34±0.23 g and 11±2.1 mm in length; and (D)*Allium sativum* var. 'ophioscorodon' subvariety Ferganski (Accession number W6 1885). Bulbils were 0.01±0.007 g and 3.1±1.4 mm in length.

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a bulbil" includes single or plural bulbils and is considered equivalent to the phrase "comprising at least one bulbil" or to the phase "comprising one or more bulbils." The term "or" refers to a single element of stated alternative elements or a combination of two or more elements, unless the context clearly indicates otherwise. As used herein, including is broadly defined to mean comprises. Also, "comprising A or B," means any or all of: A, B, or A and B," without excluding the possibility of additional elements.

Administer: To introduce an agent into a subject, such as a human subject. Methods of introduction include, but are not limited to, intradermal, intramuscular, intraperitoneal, intravenous, subcutaneous, intranasal, and oral routes. In one example green garlic is administered orally, for example in a food product. In another example, an extract of green garlic is administered, for example by ingestion, infusion or bolus injection (such as iv or ip administration), by absorption through epithelial or mucocutaneous linings (such as oral, rectal or intestinal mucosa).

Allicin: Diallyl thiosulfinate (thio-2-propene-1-sulfinic acid S-allyl ester). Includes both the R- and L-forms of allicin, as well as derivatives thereof, such as ajoene. Allicin can be produced from both the L form and the R form of alliin by allinase.

Bulbil: An asexual reproductive structure produced on scapes of maturing hardneck garlic plants. The number and size of bulbils produced by a hardneck garlic can depend on the type or variety of garlic. For example, the rocambole garlic type generally produces low numbers of large bulbils, while the porcelain garlic type typically produces hundreds of small bulbils. In particular examples, the size of the bulbil is directly related to the size of the plantlet grown from the bulbil. It is disclosed herein that bulbils can be germinated and grown quickly to produce green garlic.

Chronic pulmonary disease: A disorder of the lungs, such as those characterized by one or more of shortness of breath, coughing, sputum production, airflow limitation, and impaired gas exchange. Particular examples of such disorders include, but are not limited to: asthma, emphysema, and chronic bronchitis Food product: Any ingestible preparation, such as the green garlic disclosed herein, or extracts or preparations made from green garlic. In particular examples, the food product is one that includes green garlic, such as salads, soups, entrees, and sandwiches that include the green garlic of the present application. In some examples, the food product containing the green garlic is not exposed to temperatures that substantially reduce the presence of thiosulfinates. In another particular example, the food product is heated (for example cooked, baked or boiled) prior to adding fresh (non-cooked) green garlic to the food product. In particular examples, such food products are capable of delivering one or more thiosulfinates to a subject ingesting the food product.

Germinate: To begin to grow, such as the initiation of root and shoot development from a bulbil.

Green garlic: A plantlet produced by a bulbil. Can include the plantlet itself, or in some examples includes the plantlet attached to the bulbil. Includes extracts prepared from green garlic, such as those that include sulfur-containing compounds, for example one or more thiosulfinates.

Growth media: A substance or preparation used for the cultivation of plants or parts thereof, such as one that permits growth of green garlic from a bulbil planted in the growth media. Media can be organic or non-organic. In particular examples, media includes nutrients for the plants or parts thereof. Examples of materials that can be present in media, include, but are not limited to: lime, peat moss, and bark.

Harvest: To gather a product, such as a crop. In a particular example, green garlic is harvested, for example by removing the bulbil and the green garlic plantlet from its growth media. In another example, harvesting includes cutting or otherwise removing green garlic plantlets from germinated bulbils.

Hardneck garlic: A type of garlic that produces a flower stalk. Also referred to in the literature as "bolting" or "stalking" garlic types. One particular example of a hardneck garlic is *Allium sativum* L., such as members of the variety 'ophioscorodon', and members of the variety 'sativum'.

Particular examples of the variety ophioscorodon include, but are not limited to: *Allium sativum* variety 'ophioscorodon' subvariety Music; *Allium sativum* variety 'ophioscorodon' subvariety Red Rezan; *Allium sativum* variety 'ophioscorodon' subvariety Georgia Crystal; *Allium sativum* variety 'ophioscorodon' subvariety German Red; and *Allium sativum* variety 'ophioscorodon' subvariety Roja.

Particular examples of the variety *sativum*, include, but are not limited to: *Allium sativum* variety '*sativum*' subvariety 851004-1; *Allium sativum* variety '*sativum*' subvariety Jian Shang Dong; *Allium sativum* variety '*sativum*' subvariety Asian Tempest; *Allium sativum* variety '*sativum*' subvariety Montana Roja; *Allium sativum* variety '*sativum*' subvariety Poodles; and *Allium sativum* variety '*sativum*' subvariety 135-85-76.

Another example of a hardneck garlic are members of *Allium longicuspis* L., such as, *Allium longicuspis* 850904-42; *Allium longicuspis* PI 493097-18; *Allium longicuspis* PI 493097-47.

Large scale or commercial production: The generation of a crop for wholesale or commercial sale, such as a crop that is at least 0.1 acres, such as at least 1, at least 10, at least 100, or at least 1000 acres. Such acreage can be present in a single plot, or over several smaller plots. In one example, commercial production results in at least 100 pounds of green garlic in one year, such as at least 500 pounds, at least 1000 pounds, or even at least 5000 pounds. In a particular example, such production includes any amount of production of green garlic by a commercial grower grown for sale (in contrast to an individual grower growing green garlic for their own use).

Plantlet: A growth produced following planting a bulbil, such as at least 30 days following planting.

Subject: Living multi-cellular vertebrate organisms, including human and veterinary subjects. Particular examples of veterinary subjects include domesticated animals (such as cats and dogs), livestock (for example, cattle, horses, pigs, sheep, and goats), laboratory animals (for example, mice, rabbits, rats, gerbils, guinea pigs, and non-human primates), as well as birds, reptiles, and fish.

Therapeutically effective amount: An amount of a preparation that alone, or together with an acceptable carrier or one or more additional therapeutic agents, induces the desired response. A therapeutic agent, such as a thiosulfinate, is administered in therapeutically effective amounts.

Effective amounts a therapeutic agent can be determined in many different ways, such as assaying for a reduction in vascular or pulmonary disease, assaying for improvement of physiological condition of a subject having vascular or pulmonary disease, or assaying for an amount of anti-oxidant activity in a subject. Effective amounts also can be determined through various in vitro, in vivo or in situ assays.

Therapeutic agents can be administered in a single dose, or in several doses, for example daily, during a course of treatment. In one example, a mammal consumes a therapeutic amount of green garlic, for example daily, weekly, or monthly. However, the effective amount of can depend on the subject being treated, the severity and type of the condition being treated, and the manner of administration.

In one example, it is an amount sufficient to partially or completely alleviate symptoms of a pulmonary disease, vascular disease, cancer, or combinations thereof within a subject. Treatment can involve only slowing the progression of the disease temporarily, but can also include halting or reversing the progression of the disease permanently. For example, administration of green garlic or an extract thereof can decrease one or more symptoms of a disease (such as a vascular or pulmonary disease, or cancer), for example decrease a symptom by at least 10%, at least 20%, at least 30%, at least 50%, or even at least 90%, as compared to an amount in the absence of the green garlic (or an extract thereof).

Thiosulfinate: Includes any compound having a thiosulfinate group (O=S—S). Examples include, but are not limited to, allicin (diallyl thiosulfinate) and its related metabolites, such as allyl methyl thiosulfinate, methyl allyl thiosulfinate, ajoene, alliin, deoxyalliin, diallyl disulfide, and diallyl trisulfide.

Treating a disease: "Treatment" refers to a therapeutic intervention that ameliorates a sign or symptom of a disease or pathological condition, such a sign or symptom of vascular or chronic pulmonary disease or cancer. Treatment can also induce remission or cure of a condition, such as vascular or chronic pulmonary disease or cancer. In particular examples, treatment includes preventing a disease, for example by inhibiting the full development of a disease, such as preventing development of vascular or chronic pulmonary disease or cancer. Prevention of a disease does not require a total absence of disease. For example, a decrease of at least 50% can be sufficient.

Vascular disease: A disorder of the vascular system, such as a disease of the arteries or veins. In some examples, a vascular disease restricts blood flow to organs (such as the heart, brain, and kidneys), or to the outer extremities. Restriction of blood flow caused by a vascular disease can occur because of a buildup of cholesterol and other substances (such as fat) that block blood vessels.

Particular examples include but are not limited to, cardiovascular disease (such as hypertension (high blood pressure), coronary heart disease, cerebrovascular disease (such as a stroke), peripheral vascular disease, heart failure), renal disease, venous thrombosis, and erectile dysfunction (ED).

Green Garlic and Methods of its Production

Disclosed herein are methods of producing green garlic, a new vegetable commodity. In particular examples, the methods permit cost effective, year round commercial production of green garlic.

In one example, the method includes growing a hardneck garlic bulbil and harvesting the resulting green garlic. Hardneck garlic flowers produce clusters of bulbils on scapes of maturing plants. When these plants flower they produce a scape in the summer and vegetative bulbils in the place of true flowers. Garlic farmers remove the scapes to allow the cloyed garlic product to reach its maximum size at maturity for the crop. The present application therefore provides a new use for previously discarded bulbils. In one example, the method includes air-drying harvested bulbils to cure, and then incubating the dried bulbils under conditions that break bulbil dormancy. The non-dormant bulbils can then be planted for growth of green garlic.

In particular examples, the disclosed methods provide a cost-effective method of producing large quantities of green garlic. Green garlic has been produced at a cost of about 1.2 cents per plant. However, in other examples, green garlic is produced at no more than 1.2 cents per plant, such as at a cost of about 0.001 cents per plant, such as no more than 0.001 cents per plant. In yet another example, green garlic can be produced at a cost of 0.001-1.2 cents per plant. In a desired example, such costs include the total cost of production, such as bulbil production, water costs, greenhouse costs, growth medium costs, and labor.

In one example, the disclosed methods provide the ability to produce commercial amounts of green garlic year-round. Commercial production includes any crop or production of green garlic by a commercial grower (for example one who produces green garlic for wholesale or commercial sale), as contrasted to individual growers growing green garlic for their own private or personal use. In a specific example, commercial amounts of green garlic include plants from a large crop, such as a crop that produces at least 100 pounds of green garlic annually, such as at least 200 pounds, at least 500 pounds, at least 1000 pounds, or even 10,000 pounds annually. In another specific example, commercial production includes production from a crop grown in a plot size is at least 0.1 acres, such as at least 1 acre, at least 10 acres, at least 100 acres, or even at least 1000 acres. Such plots can be present as a single plot, or divided over two or more plots.

In particular methods, the method of producing green garlic includes planting the hardneck garlic bulbil under conditions that result in germination of the bulbil, and harvesting the green garlic generated from the bulbil. It has been observed that the size of the bulbil correlates to the size of the plantlet produced from the bulbil. For example, small bulbils produce sprout-like green garlic (FIG. 1D), medium sized bulbils produce scallion-like garlic (FIGS. 1B, 1C), and larger bulbils produce leek-like green garlic (FIG. 1A).

In some methods, the bulbils are planted at a particular density, such as an average density of 2 million bulbils per acre, such as at least 2 million bulbils per acre, for example 2-5.5 million bulbils per acre, for example 2-5.5 million bulbils per acre of *Allium sativum* variety 'ophioscorodon' subvariety Music (Accession number PI 515972). In a specific example, bulbils are planted at an average density of at least 100 per 2 ft by 2 ft area, such as at least 200 bulbils per 2 ft by 2 ft area, for example 100-500 bulbils per 2 ft by 2 ft area.

In another method, hardneck garlic varieties with large bulbils are planted at a lower density, such as an average density of 1 million bulbils per acre, such as at least 1 million bulbils per acre, for example 1-5 million bulbils per acre. In a particular example, 1-5 million bulbils of *Allium sativum* var. 'ophioscorodon' subvariety Blanco De Huelma Zamora (Accession number PI 615423) are planted per acre.

In yet another example, hardneck garlic varieties with small bulbils are planted at a higher density, such as an average density of 4 million bulbils per acre, such as at least 4 million bulbils per acre, for example 4-10.5 million bulbils per acre. In a particular example, 4-10.5 million bulbils of *Allium sativum* var. 'ophioscorodon' subvariety Ferganski (Accession number W6 1885) are planted per acre.

In some examples, prior to planting harvested bulbils, the bulbil is exposed to conditions that break bulbil dormancy, for example exposing the bulbil to a cold temperature for a time sufficient to break bulbil dormancy, such as a period of at least 25 days, at least 30 days or at least 35 days. In a particular example, the bulbil is exposed to a temperature below 15° C., such as below 10° C., below 5° C., no more than 4° C., for example O-15° C., or 0-4° C., such as 4° C. In one example, the bulbil is incubated at 0-15° C. (such as 0-4° C.) for at least 25 days, such as at least 30 days, prior to planting.

In particular examples, bulbils are harvested from a hardneck garlic scape, sized, and incubated under conditions that terminate bulbil dormancy (for example as described above). Sizing bulbils can include sorting bulbils according to their length or weight, such as sorting into populations of small, medium, and large bulbils. In particular examples, the resulting population of bulbils are within 2-6 mm in length of each other for large bulbils, within 2-3 mm in length of each other for medium bulbils, and within 1-2 mm in length of each other for small bulbils. In particular examples, the resulting population of bulbils is within 0.1-0.9 g of each other for large bulbils, within 0.01-0.09 g of each other for medium bulbils, and within 0.001-0.009 g of each other for small bulbils. In some examples, bulbils are dried after harvest, and before incubation under conditions that terminate bulbil dormancy.

Bulbils can be grown indoors, for example in a greenhouse or a hoop house, or outdoors (such as in climates that permit year-round growth of bulbils, for example southern climates, such Florida, Southern California, and Mexico). Growing bulbils indoors allows for greater control of pathogens and environmental conditions (such as regulation of temperature, irrigation, fertilization and pesticides). For example, the green garlic vegetable is susceptible to a variety of pathogenic pest infestations. Treatment of such pests can cost more than the product is worth. In addition, excessive heat (such as temperatures of at least 85° F.) during summer months can create tip burn that increases the time required to harvest the green garlic (since ideally the burned tips are removed). If desired, a shade cloth can be used as a deterrent to tip burn during times of increased sunlight and heat. In one example, plants grown indoors (for example in a greenhouse) are tenderer than those grown outdoors.

Bulbils can be grown in any appropriate growth medium that allows for the growth of the green garlic. In particular examples, bulbils are grown in an organic substrate. If desired, growth conditions can be optimized for particular hardneck varieties. Methods of determining such parameters, such as growth medium composition, lighting conditions, water, temperature conditions, and nutrient growth additives, are known in the art. In addition, exemplary methods are provided herein.

Harvesting the green garlic from the bulbil can include obtaining the produced green garlic. In one example, harvesting includes removing the entire plant (the green garlic and the bulbil) from the growth medium. In another example, harvesting the green garlic includes removes the green garlic from the bulbil, such as cutting. In particular examples, the green garlic is harvested from the bulbil at least 20 days after planting and germination of the bulbil, such as at least 30 days, or at least 40 days, such as 30-45 days following planting and germination of the bulbil.

The resulting harvested green garlic can be sold directly. In one example, the method of the present disclosure includes packaging the harvested green garlic in a container, such as a container suitable for shipping the green garlic, storing the green garlic, selling the green garlic (or combinations thereof). In a particular example, green garlic is packaged into a container, such as a bag or box, for sale. In another example the container can be a pot, tray, or bowl, for example for sale as a starter plant for a home gardener. In another example, green garlic is combined with other products, such as salad greens. Such combinations can also be packaged for sale.

Methods for producing a food product that includes one or more sulfur-containing compounds, such as one or more thiosulfinates are disclosed. In particular examples the method includes germinating a bulbil and harvesting the green garlic to form a food product that includes one or more sulfur-containing compounds. In one example, such production is commercial production, which is ideally cost-effective. The method can also include planting the bulbils. Particular examples of sulfur-containing compounds include thiosulfinates and derivates thereof, such as thio-2-propene-1-sulfinic acid S-allyl ester (allicin) S-allyl cysteine sulphoxide (alliin), S-methyl cysteine sulphoxide (methiin), trans S-1-propenyl cysteine sulphoxide (isoalliin), S-propyl cysteine sulphoxide (propiin), as well as combinations thereof. As disclosed above, such methods can also include one or more of harvesting the bulbils, drying the bulbils, sizing the bulbils, and breaking the dormancy of the bulbils, prior to planting the bulbil.

Bulbils

In some examples, the bulbils are of a uniform size, such as a uniform length, uniform weight, or combinations thereof. The use of uniformly sized bulbils allows for the production of a more uniform crop of green garlic. In a particular example, a uniform population of bulbils is one wherein the length of the bulbils is uniform, such as a population within one millimeter of each other, such as within 0.5 mm of each other, such as within 0.1 mm of each other. In particular examples, the population of bulbils is within 2-6 mm in length of each other for large bulbils, within 2-3 mm in length of each other for medium bulbils, and within 1-2 mm in length of each other for small bulbils. In another example, a uniform population of bulbils is one wherein the weight of the bulbils is uniform, such as a population within 2 g of each other, such as within 1 g of each other, such as within 0.1 g of each other, or as within 0.01 g of each other. In particular examples the population of bulbils is within 0.1-0.9 g of each other for large bulbils, within 0.01-0.09 g of each other for medium bulbils, and within 0.001-0.009 g of each other for small bulbils.

Although particular methods of generating such populations are disclosed herein, the disclosure is not limited to such methods. In one example, the method includes passing bulbils through screens or other materials having particular diameter openings, allowing bulbils of only particular size to pass through. This allows for collection or isolation of bulbils of a particular size. In other example, a machine is used to sort bulbils by size or by weight. In yet another example, gravity is used, wherein the larger heavier bulbils will sink more quickly than smaller lighter bulbils.

In a particular example, the bulbil is a small bulbil. Such bulbils, for example those from *Allium sativum* var. 'ophioscorodon' subvariety Ferganski (Accession number W6 1885), can be used to produce sprout-like green garlic. In one example a small bulbil is one less than 3.5 mm in length, such as one that is about 1.0-3.4 mm in length or 1.5-3.4 mm in length. In a specific example, a population of small bulbils includes bulbils that are 0.4-3.4 mm in length, or 0.9-2 mm in length. In another example a small bulbil is one less than 0.039 g, such as one that is about 0.01-0.025 g or 0.005-0.025 g. In a specific example, a population of small bulbils includes bulbils that are 0.01-0.03 g.

In another example, the bulbil is a medium-sized bulbil. Such bulbils, for example those from *Allium sativum* var. 'ophioscorodon' subvariety Music (Accession number PI 515972), can be used to produce scallion-like green garlic. In one example a medium-sized bulbil is one that is 3.5-8.9 mm in length, such as 4 mm-6 mm in length, 5 mm-6 mm in length, 3.5 mm-4.5 mm in length, or 5.5-6.5 mm in length. In a specific example, a population of medium-sized bulbils includes bulbils that are 3.5-4.5 mm in length, 4.5-5.5 mm in length, 5.5-6 mm in length, 5-6 mm in length, 4.5-5.5 mm in length. 3.5-4 mm in length, or 4-5 mm in length. In another example a medium-sized bulbil is one 0.04-0.29 g, such as 0.05-0.1 g, or 0.5-0.2 g.

In yet another example, the bulbil is a large bulbil. Such bulbils, for example those from *Allium sativum* var. 'ophioscorodon' subvariety German Red (Accession number PI 540538), can be used to produce leek-like green garlic. In one example a large bulbil is one at least 9 mm in length, such as one that is about 9-13 mm in length or 9-15 mm in length. In a specific example, a population of large bulbils includes bulbils that are 9-10 mm in length, or 9.5-10.5 mm in length. In another example a large bulbil is one at least 0.3 g, such as one that is about 0.3-1 g or 0.3-0.6 g. In a specific example, a population of large bulbils includes bulbils that are 0.3-2 g.

Hardneck Garlic Varieties

Hardneck varieties of garlic are known. In one example, the bulbil is an *Allium longicuspis* L. bulbil, or a *Allium sativum* L. bulbil, such as a member of the 'ophioscorodon' variety or the variety '*sativum*'.

Particular examples of 'ophioscorodon' subvarieties include, but are not limited to: *Allium sativum* variety 'ophioscorodon' subvariety Music; *Allium sativum* variety 'ophioscorodon' subvariety Red Rezan; *Allium sativum* variety 'ophioscorodon' subvariety Georgia Crystal; *Allium sati-*

*vum* variety 'ophioscorodon' subvariety German Red; and *Allium sativum* variety 'ophioscorodon' subvariety Roja.

Particular examples of the variety '*sativum*', include, but are not limited to: *Allium sativum* variety '*sativum*' subvariety 851004-1; *Allium sativum* variety '*sativum*' subvariety Jian Shang Dong; *Allium sativum* variety '*sativum*' subvariety Asian Tempest; *Allium sativum* variety '*sativum*' subvariety Montana Roja; *Allium sativum* variety '*sativum*' subvariety; Poodles; and *Allium sativum* variety '*sativum*' subvariety 135-85-76.

Food Products

The green garlic vegetable produced by the disclosed methods, as well as extracts thereof, are also provided by this application. In particular examples, the green garlic is raw, for example not exposed to conditions that would significantly destroy the thiosulfinates present in the green garlic (for example not reduce the presence of one or more active thiosulfinates by more than 50%). If green garlic is exposed to an elevated temperature, for example to wash the green garlic, it is ideally done so for a short period of time to reduce the loss of thiosulfinates. In a particular example, green garlic is not exposed to temperatures involved in cooking (such as baking, broiling or frying). In a specific example, the green garlic is not exposed to a temperature that exceeds 170° F. for longer than 5 minutes, such as no more than 3 minutes, such as no more than 1 minute, prior to consumption (or other form of administration).

The disclosed green garlic food products can be consumed alone, or in the presence of other food products containing the green garlic. Food products that include the disclosed green garlic are also provided by the present disclosure. Particular examples of such food products, include, but are not limited to salad, soup, appetizers, and entrees. In one example, raw or uncooked green garlic is added to another food product, such as another raw food product (such as a salad) or a food product that has been cooked. In some examples, the green garlic is dehydrated, for example formed into a powder (for example for green garlic powder or green garlic pills. In some examples, extracts of green garlic are obtained, for example for use in an oil, such as olive oil.

In particular examples, the green garlic of the present application includes sulfur-containing compounds, such as thiosulfinates, for example allicin and derivatives thereof. In some examples, the green garlic includes at least 0.1 mg of allicin per gram of green garlic, at least 0.1 mg S-methyl cysteine sulphoxide (methiin; AllS(O)SMe) per gram of green garlic, at least 0.1 mg trans S-1-propenyl cysteine sulphoxide (isoalliin) per gram of green garlic, at least 0.1 mg S-propyl cysteine sulphoxide (propiin: AllS(O)SPropenyl) per gram of green garlic, or combinations thereof, for example from *Allium sativum* var. 'ophioscorodon' subvariety Music (Accession number PI 515972), for example measured by HPLC after 30-45 days of growth. In a specific example, the green garlic of the present application is from a *Allium sativum* var. 'ophioscorodon' subvariety Music bulbil, and includes 0.5-4.0 mg of allicin per gram of green garlic, 0.1-1.0 mg S-methyl cysteine sulphoxide (methiin; AllS(O)SMe) per gram of green garlic, 0.1-1.0 mg trans S-1-propenyl cysteine sulphoxide (isoalliin) per gram of green garlic, and 0.1-1.0 mg S-propyl cysteine sulphoxide (propiin: AllS(O)SPropenyl) per gram of green garlic after 30-45 days of growth, for example measured by HPLC. In a particular example, an extract of green garlic contains one or more thiosulfinates, such as a concentrated amount of thiosulfinates.

Methods for making plant extracts are known. In a particular example, an extract or homogenate of green garlic, for example to determine an amount of one or more thiosulfinates present, such as an amount of allicin present in the green garlic, is made as follows. Green garlic (2 g) was ground in 20 ml water, centrifuged at 500 rpm for 10 minutes, the pellet is discarded and the supernatant recovered and diluted it 1:1 with water.

Methods for measuring an amount of garlic metabolite, such as allicin and derivatives thereof, present in the green garlic are known. In one example, high performance liquid chromatograph (HPLC) is used. Briefly, an extract of the green garlic is generated, for example using the method described above. A calibration curve is generated using known amounts of a thiosulfinate, such as alliin or allicin. The green garlic extract is compared to the calibration curve to determine an amount of allicin or other thiosulfinate present. Another method that can be used is reversed-phased high performance liquid chromatography coupled to mass spectrometry with multiple ions reaction monitoring.

Crops

Crops that include planted bulbils are also provided by this disclosure. In one example, a crop that produces at least 100 pounds of green garlic annually, such as at least 200 pounds, at least 500 pounds, at least 1000 pounds, or even 10,000 pounds annually. In a specific example, the disclosed crops are grown in one or more plots to form a total of at least 0.1 acres, such as at least 1 acre, at least 10 acres, at least 100 acres, or even at least 1000 acres.

Administration of Therapeutic Amounts of Sulfur-Containing Compounds

The present application provides methods of increasing the amount of one or more sulfur-containing compounds, such as one or more thiosulfinates, to a mammal, for example in the cell of such a mammal (such as a human). In one example, the amount is a therapeutic amount.

In one example, the method includes administering the disclosed green garlic or a non-toxic extract thereof to the mammal, thereby increasing the amount of one or more sulfur-containing compounds in the mammal. In one example, the green garlic includes at least 0.5 mg of allicin per gram of green garlic. In particular examples, the method includes administering a therapeutically effective amount of allicin to the mammal, for example by ingestion of at least 3.5 mg of green garlic daily, such as 3.5-25 mg daily.

Such methods can be used to treat one or more diseases in the mammal, such as a vascular disease, chronic pulmonary disease, or cancer. In specific examples, such methods lower blood pressure, decrease ischemic injury, reduce serum cholesterol, reduce platelet aggregation, decrease plasma homocysteine levels, lower the incidence of cancer, increase thrombolysis, or combinations thereof. In one example, such treatments are relative to a control, such as a subject having a similar health condition, but not administered the green garlic (or extract thereof) or other therapeutic agent.

In a specific example, the green garlic (or extract thereof) includes one or more chemoprotective compounds, which when administered to a mammal, protect coronary vascular function and lessen the severity of right heart hypertrophy, for example to treat chronic pulmonary hypertension.

Example 1

Bulbils

This example describes exemplary bulbils that can be used as a source of starting material for the production of green garlic. One skilled in the art will appreciate that other hardneck garlic varieties can be used.

Germplasm was examined for varieties that produce large numbers of bulbils. Bulbils from USDA, ARS, WRPIS (Washington State University) were harvested in the summer (July), air dried, and cold treated (4-15° C.) for 30 days, and stored in typical seed storage environments (room temperature (20-28° C.) and 20-40% relative humidity). Alternatively, bulbils can be stored in the cold (4-15° C.) or at room temperature until use without airdrying. The number of bulbils per plant is shown in Table 1 for various exemplary varieties examined to date. The size of the bulbil is directly related to the size of the plantlets that germinate.

TABLE 1

Characteristics of bulbils from hardneck garlic varieties.

| Variety | Number of Bulbils per inflorescence | Total weight of bulbils (g) | Length (mm) |
|---|---|---|---|
| Rocambole types | | | |
| 'Carpathian' | 16 | 7.1 | 13.2 ± 3.2 mm |
| 'Dominics' | 7 | 8.2 | 12.3 ± 2.7 mm |
| 'French red' | 4 | 5.0 | 11.4 ± 2.8 mm |
| 'German Red' | 9 | 8.8 | 11.0 ± 2.1 mm |
| 'Israeli' | 25 | 12.0 | 10.6 ± 3.7 mm |
| 'Legacy' | 20 | 7.2 | 14.2 ± 3.9 mm |
| 'Marino' | 16 | 6.0 | 11.1 ± 2.1 mm |
| 'Roja' | 30 | 6.6 | 13.6 ± 2.9 mm |
| 'Yerina' | 13 | 7.7 | 10.8 ± 1.8 mm |
| 'Yugoslavian' | 25 | 8.3 | 12.6 ± 2.3 mm |
| Porcelain types | | | |
| 'Georgia Crystal' | 145 | 4.3 | 6.6 ± 2.8 mm |
| 'Georgia Fire' | 207 | 6.2 | 6.6 ± 2.8 mm |
| 'Leningrad' | 302 | 10.7 | 5.5 ± 1.9 mm |
| 'Music' | 243 | 8.4 | 6.0 ± 2.4 mm |

TABLE 1-continued

Characteristics of bulbils from hardneck garlic varieties.

| Variety | Number of Bulbils per inflorescence | Total weight of bulbils (g) | Length (mm) |
|---|---|---|---|
| 'Red Rezan' | 104 | 3.2 | 7.4 ± 2.9 mm |
| 'Weingarten' | 61 | 10.6 | 8.1 ± 3.4 mm |

Example 2

Cold Treatment to Break Bulbil Dormancy

This example describes methods used to determine an optimum temperature and incubation time to terminate dormancy of the bulbils. One skilled in the art will appreciate that similar methods can be used to determine the optimum dormancy temperatures and times for other bulbil varieties.

Methods were performed to calculate the time needed to terminate dormancy using cold treatment, since dormancy breakage can be genotype dependent. To achieve as close to 100% germination as quickly as possible, bulbils from field grown plants were subjected to a cold treatment as follows. *Allium sativum* cv Music bulbils of varying sizes were placed into chambers at 0° C., 4° C., 15° C., or room temperature (20-28° C.) (control). Bulbils (100) were removed from each chamber at intervals of 4, 7, 14, 20, 25, 30 and 35 days. Each group was sown in standard Pro-Mix® potting soil and irrigated with equal amounts of non-fertilized water.

Table 2 shows the germination results after various lengths of cold treatment, expressed as the percentage of bulbils germinated (emergence) as a function days after planting (4, 7, 14, 20, 25, 30, or 35 days after planting). Percentages were based on total number planted divided by total number emerged. As used herein, germination is the initiation of root and shoot.

TABLE 2

Effect of time of cold treatment on breaking bulbil dormancy

| | % Emergence after # of Days post-planting | | | | | | |
|---|---|---|---|---|---|---|---|
| | 4 days | 7 days | 14 days | 20 days | 25 days | 30 days | 35 days |
| 0° C. for 4 days | 0 | 0 | 0 | 0 | 12 | 21 | 34 |
| 0° C. for 7 days | 0 | 0 | 5 | 15 | 27 | 40 | 45 |
| 0° C. for 14 days | 0 | 0 | 25 | 33 | 42 | 61 | 61 |
| 0° C. for 20 days | 0 | 0 | 25 | 41 | 58 | 64 | 71 |
| 0° C. for 25 days | 0 | 90 | 95 | 98 | 98 | 98 | 98 |
| 0° C. for 30 days | 8 | 99 | 99 | 99 | 99 | 99 | 99 |
| 0° C. for 35 days | 5 | 99 | 99 | 99 | 99 | 99 | 99 |
| 4° C. for 4 days | 0 | 0 | 0 | 0 | 15 | 23 | 35 |
| 4° C. for 7 days | 0 | 0 | 0 | 14 | 28 | 38 | 49 |
| 4° C. for 14 days | 0 | 0 | 19 | 32 | 44 | 58 | 64 |
| 4° C. for 20 days | 0 | 0 | 25 | 41 | 58 | 64 | 71 |
| 4° C. for 25 days | 0 | 92 | 95 | 98 | 98 | 98 | 98 |
| 4° C. for 30 days | 5 | 98 | 99 | 99 | 99 | 99 | 99 |
| 4° C. for 35 days | 5 | 98 | 99 | 99 | 99 | 99 | 99 |
| 15° C. for 4 days | 0 | 0 | 0 | 0 | 10 | 13 | 25 |
| 15° C. for 7 days | 0 | 0 | 0 | 13 | 18 | 34 | 36 |
| 15° C. for 14 days | 0 | 0 | 9 | 27 | 34 | 48 | 52 |
| 15° C. for 20 days | 0 | 0 | 28 | 39 | 46 | 61 | 70 |
| 15° C. for 25 days | 0 | 72 | 84 | 81 | 78 | 82 | 88 |
| 15° C. for 30 days | 3 | 80 | 80 | 82 | 80 | 84 | 89 |
| 15° C. for 35 days | 8 | 95 | 95 | 96 | 95 | 95 | 95 |
| 25° C. for 4 days | 0 | 0 | 0 | 0 | 0 | 0 | 0 |
| 25° C. for 7 days | 0 | 0 | 0 | 0 | 0 | 0 | 0 |
| 25° C. for 14 days | 0 | 0 | 0 | 0 | 0 | 0 | 0 |
| 25° C. for 20 days | 0 | 0 | 0 | 0 | 0 | 0 | 0 |
| 25° C. for 25 days | 0 | 0 | 0 | 0 | 0 | 0 | 0 |
| 25° C. for 30 days | 0 | 0 | 0 | 0 | 0 | 0 | 0 |
| 25° C. for 35 days | 0 | 0 | 0 | 0 | 0 | 0 | 0 |

Based on these observations, bulbils can be desirably stored at 0° C. or 4° C. for 30 days to terminate dormancy, and allow for at least 98% germination within 7 days. It is expected that other hardneck garlics will have a similar response to incubation at cold temperatures.

Once the bulbils have satisfied their dormancy periods, additional refrigeration is ideally avoided because of the increased risk of excessive moisture exposure and eventual composting.

After exposure of 30,000 *Allium sativum* cv 'Music' bulbils to 4° C. for 30 days, bulbils were placed in trays, to a depth of no more than 3 inches thick and stored in dehumidified rooms (20-50% relative humidity) at 23-25° C. A consistent 95-100% germination rate has been observed. Emergence, when the shoot has broken the soil surface usually at a height of 1 inch, occurred consistently at the 7-9 days after planting.

Example 3

Production of Green Garlic from Bulbils

This example describes methods used to produce green garlic from harvested bulbils whose dormancy had been terminated as described in Example 2. These results demonstrate that bulbils can be used as a source material for production of green garlic.

Several varieties of garlic bulbils were planted in a greenhouse (USDA Germplasm Repository in Pullman, Wash.) November 2003, and plantlets analyzed about one month later (December 2003).

The bulbils were grown from cloves planted on a nursery at the Regional Plant Introduction Station at Washington State University (Pullman, Wash.). The bulbils were harvested in the fall, and had been subjected to sufficient cold temperatures to break dormancy (see Example 2). Samples of bulbils from many germplasm sources were recovered (Table 1).

To demonstrate that bulbils can be grown to provide green garlic under greenhouse conditions, the bulbils were planted in either four or six inch pots in Pro-Mix® potting soil (1-6 bulbils per pot). The pots were watered regularly and grown with ambient greenhouse light. The temperature was maintained at 24-28° C. with a relative humidity of 80-85%. The bulbils germinated in 5-8 days and emerged as small shoots. The shoots were grown for 30-45 days and photographed.

As shown in FIGS. 1A-D, green garlic can be produced from hardneck garlic bulbils. The size of the bulbil was directly related to the size to the plantlet grown from the bulbil. For example, FIGS. 1A and 1C show a leek-like green garlic produced from large bulbils from *Allium sativum* var. 'ophioscorodon' subvariety Blanco De Huelma Zamora (Accession number PI 615423) (bulbils were 0.52±0.13 g and 14±5.4 mm in length, FIG. 1A) or *Allium sativum* var. 'ophioscorodon' subvariety German Red (Accession number PI 540538) (bulbils were 0.34±0.23 g and 11±2.1 mm in length, FIG. 1C). FIG. 1B shows a scallion-like green garlic produced from medium sized bulbils (0.05±0.033 g and 6±2.4 mm in length) from *Allium sativum* var. 'ophioscorodon' subvariety Music (Accession number PI 515972). FIG. 1D shows a sprout-like green garlic produced from small bulbils (0.01±0.007 g and 3.1±1.4 mm in length) from *Allium sativum* var. 'ophioscorodon' subvariety Ferganski (Accession number W6 1885). Therefore, different sized plants can be generated and marketed as individual products, such as sprout-like, scallion-like, and leek-like green garlic.

In addition, each variety has different growth taste and other characteristics, such as tenderness. Therefore, bulbil varieties can be selected which satisfy production standards as well as taste, texture, and other desirable qualities.

In summary, bulbils can be grown en mass from hardneck garlic cloves planted the season before, harvested, dormancy-terminated, and planted to satisfy the year-round supply for commercialization. The resulting plantlets can also be placed into pots for sale as a fresh vegetable or as a starter plant for outdoor gardens.

Example 4

Effect of Temperature and Light on Germination and Growth

This example describes methods used to determine optimal temperature and light conditions on germination and seedling growths for the *Allium sativum* cv 'Music' variety. One skilled in the art will appreciate that similar methods can be used to determine the optimum temperature and light conditions for other varieties.

*Allium sativum* cv Music bulbils (100) stored at 4° C. for 30 days (Example 2) were sown in Metro-mix® potting soil (Sun Gro Horticulture, Bellevue, Wash.) and grown in a greenhouse at temperature variations ranging from 50-60° F., 60-70° F., 70-80° F., or 90-100° F. Germination and growth rates were determined. Germination assessments were made on days 4, 6, 8, 10, 12, 14 and 16 days following planting. Percentages were based on germination rate of 100 bulbils.

As shown in Table 3, bulbils can be grown at any temperature between 50-80° F., although warmer temperatures produced greater numbers of germinated plants more quickly. Therefore, green garlic is desirably grown at temperatures of 70-80° F. However, temperatures in the range of 90-100° F. were detrimental to plant growth.

TABLE 3

Effect of temperature on growth and germination.

| | % Germination | | | | | | |
|---|---|---|---|---|---|---|---|
| | 4 days | 6 days | 8 days | 10 days | 12 days | 14 days | 16 days |
| Sown @ 50-60° | 0 | 0 | 0 | 5 | 15 | 42 | 61 |
| Sown @ 60-70° | 0 | 29 | 52 | 71 | 79 | 82 | 89 |
| Sown @ 70-80° | 0 | 59 | 78 | 91 | 97 | 97 | 97 |

In addition to temperature, the effect of light was also examined. Bulbils were planted and grown in a greenhouse at 70-80° F. in the presence of halogen lamps suspended 3 meters above growing plants for various periods of time from 1-24 hrs. Supplemental light positively affected growth. It was observed that 14-24 hrs of direct light slightly increased growth rate. A light regime of 12-14 hrs was sufficient for seedling growth, but at a slightly diminished rate in contrast with 14-24 hrs.

Therefore, when grown indoors, such as in a greenhouse, production of green garlic can be increased by providing supplemental lighting (natural or artificial) for 14-24 hrs.

Example 5

Effect of Growth Media on Germination and Growth

This example describes methods used to determine the effect of organic and inorganic growth media on germination and seedling growth. One skilled in the art will appreciate that similar methods can be used to determine the effect of organic and inorganic growth media for other garlic varieties.

Non-organic and organic growth media were produced as follows. For a 1 yard supply non-organic growth media, trays were filed ⅔ full with the following potting mix: 3 parts peat moss (Farford Inc.), 4 parts aged southern pine bark (Farford Inc.), 5 parts Styrofoam, 425 grams of Rootshield® (Bio-Works, Inc., Fairport, N.Y.), 425 grams of lime, 425 grams of Osmocote® 22-3-8 (Scotts, Marysville, Ohio), and 215 grams micro-nutrient. Once bulbils broadcast, they were covered with the following mixture (makes 21 yards): 7 yards aged pine bark, 6 yards non aged pine bark, 2 yards peat moss, 3 yards course sand, 80 lbs lime, 160 lbs Osmocote® 22-3-8, and 40 lbs Microboost™.

Another non-organic growth media used is as follows (this made ½ cubic yard of green garlic growth media): 3 cubic feet peat moss (Farford Inc.), 4 cubic feet aged pine bark (Farford Inc.), 20 lb bag of medium grade perlite (Whittemore Inc., Lawrence, Mass.), ½ lb Micromax® micronutrient fertilizer in granular form (Scotts), 1 lb Rootshield® biological fungicide (BioWorks, Inc.), 1 lb lime, 1 lb Actino Iron® 0-0-0 fungicide (Natural Industries Inc., Houston, Tex.), 1 lb Osmocote® 19-6-12 non-organic fertilizer (Scotts), ZeroTol® broad spectrum algacide (Biosafe Systems Inc., Glastonbury, Conn.) at ratio of 100 ppm, and Peter's Professional Water Soluble Fertilizer (Scotts) (water soluble fertilizer 20-9-20) at a ratio of 1 to 100 ppm.

For a 1 yard supply organic growth media, trays were filled ⅔ full with the following potting mix: 3 parts southern aged pine bark, 4 parts peat moss, 5 parts medium grade perlite, 425 g of Rootshield® biological fungicide, 425 g of lime, and 215 g micro nutrient. Once bulbils broadcast, they were covered with: 8 yards ½-5-8 inch grades southern pine bark, 2 yards of course sand, 25 ft3 peat moss, 15 ft3 Rootshield® biological fungicide, and 80 lbs lime.

Plants grown in accordance with USDA Certified Organic standards were produced in the organic media with all other treatments being equal to those developed for non-organically produced plants. Plants produced without the organic considerations are referred to as 'non-organic' methods.

The tray was filled ⅔ full with organic or non-organic potting mixture, and the bulbils sown at a density of 100-500 bulbils per tray. Bulbils were sown either root-down (as with their garlic clove relatives), or via broadcast planting (random scattering rather than planting in rows). The root-down method of planting bulbils was time consuming and did not offer a significant a benefit compared with broadcast planting. Robotic planting overcomes this problem. After planting and adequately spacing the bulbils (a density of 200-500 plants spread evenly over 4 sq ft.), the covering mixture was used to cover with tray at a depth no more than the length of the bulbils sown. Generally, this depth averaged ¼ inch. Green garlic was grown in a greenhouse and was ready for harvesting within 30-45 days following planting.

In one example, bulbils were grown outdoors (Lebanon, Conn. and at The University of Rhode Island). Plants can be grown outdoors in climates where this is possible, such as locations where temperatures are between 60-85° F. One method used large open tables. Large amounts of soil were required, and germination times increased to 5-10 days. Another outdoor method used raised beds or benches filled with black polypropylene trays. This method permitted direct solar radiation. In addition, polypropylene trays allowed for better manipulation and manageable cleanup during harvest. Flat fillers permit automated filling of the trays. Growing this crop at floor level invites the risk for standing water which tends to promote plant diseases.

Therefore, green garlic can be grown in outdoor conditions in climates where this is appropriate. Outdoor conditions can be used to produce organically grown as well as non-organically grown green garlic. However, no substantial differences have been observed for green garlic grown organically or non-organically. Although growth of plants outdoors can reduce the cost of producing green garlic, such outdoor methods can not be accomplished year round due to cold temperatures. In climates that do not support outdoor growing conditions, year round growth can be achieved in a greenhouse.

Density of bulbils planted can be a factor in successful growth and production of green garlic. If bulbils are sown at a high density, competition and weediness can result. Too bulbils are sown at a low density, wasted space, low yields and lost revenue can result. Based on the dimensions of the growing trays used herein, a density of 100-500 bulbils per 4 sq ft approach high density.

Other growth conditions investigated included irrigation methods, fertilizers and use of organic and non-organic pesticides as well as pest management solutions.

Irrigation: Bulbils need to be watered regularly after planting. Ideally, the soil is well drained and just allowed to dry before re-watering. In one example, for example when the bulbils are grown indoors, overhead irrigation is used, such as the Rainbird® 1800 U-series nozzles. This product offers a 6 ft wide square pattern of coverage with the addition of an extra port for close-in watering.

Fertilizers: For inorganic growing, 10-10-10 liquid fertilizer can be used. Use of a 20-20-20 type results in a stem that is too small to support the weight of the plant once the plant reaches 12 inches. For organic growing, an organic fertilizer made from North Atlantic fish (such as Neptune's Harvest Liquid Fish plant food 2-4-0.5) can be used.

Organic Pesticide: ZeroTol® is an all purpose, contact fungicide/algaecide that can be included at a 1:1000 rate to maintain good plant heath. Fertilization and introduction of organic pesticides can be well achieved with the use of Dosatron® injectors set at the appropriate manufacture ratios (Dosatron International, Clearwater, Fla.).

Integrated Pest Management: Green garlic was extremely susceptible to pests, such as fungus gnats and Western flower thrips. Fungus gnats in maggot form burrow into the bulbils eventually hollowing the bulbils. Thrips tend to present with blotchy white streaks along the plant. Beneficial insects have been used rather than pesticides and can be incorporated into the planting regime to avoid costly and potentially large scale damage to the crop.

Example 6

Greenhouse Production

This example provides methods for producing commercial amounts of green garlic in a greenhouse. For example, bulbils of various varieties (and sizes) can be planted and grown to a market size within 30 days.

Bulbils were grown in the greenhouse, for example in containers, on raised beds or directly in the ground. Greenhouse growth can provide certain advantages including controlled and uniform growing conditions, diminished exposure to pests and diseases, and ease of harvest.

Harvest of Bulbils

Bulbils (see Table 1) were harvested from mature plants in late summer or early autumn. The inflorescences were cut and placed in bags that retained loose bulbils. The bulbils were removed from the inflorescence and the stalk discarded. The loose bulbils were then dried and stored.

Drying of Bulbils

The bulbils were dried in trays or in bulk at 24-28° C. and 30-55% relative humidity for thirty days.

Sizing of Bulbils

Bulbils are sorted by size/weight. Generally, for *Allium sativum* ophioscorodon cv Music where larger bulbils reach plantlet maturity in 30-45 days, medium size bulbils mature in 30-70 days. Seed grading will actively encourage consistency as well as competitiveness of seedlings. There are many commercial ways to successfully grade out bulbils. However, the use of nylon or wire screens is a cheap and effective way of grading bulbils.

Planting Bulbils

Bulbils of the appropriate size are planted according to the desired product. Larger bulbils have greater vigor and emerge faster, whereas medium size bulbils while over time eventually reach marketable height, have longer emergence times and longer periods to grow.

Bulbils are planted in trays and grown in a greenhouse or polyhouses. Bulbils can be grown at an average density of fifty-five hundred plants per 2 ft by 1 ft flat. This converts to two million plants per month in a 100 ft polyhouse. Bulbils can be planted in organic or non-organic medium as described above.

Temperature is maintained between 70-85° F., and supplemental lighting is used to increase the time and intensity of light received by the developing plants (for example lighting for 14-24 hrs). Watering is provided regularly in a mist type bench, and can include ZeriTol® fungicide, fertilizers or other watering additives that facilitate growth. A crop per acre (44,000 sq ft) of greenhouse space can produce 5.5 million plants per 30-45 day cycle from as many bulbils.

Harvesting Green Garlic

Plants can be harvested by any method known in the art, such as by machine or by hand. The resulting green garlic plants can be sold directly, or packaged into appropriate packaging or containers for shipping or sale.

Example 7

Measurement of Thiosulfinates in Green Garlic

This example describes methods used to determine the concentration of thiosulfinate compounds present in the green garlic of the present application.

HPLC analysis was used to compare the allicin content, and derivatives thereof such as alk(en)yl cysteine sulphoxides including; S-allyl cysteine sulphoxide (allicin), S-methyl cysteine sulphoxide (methiin; AllS(O)SMe), trans S-1-propenyl cysteine sulphoxide (isoalliin) and S-propyl cysteine sulphoxide (propiin: AllS(O)SPropenyl) in green garlic plantlets, bulbils and garlic cloves of *Allium sativum* ophioscorodon cv. Music.

Green garlic (2 g) generated 30-45 days after planting bulbils was ground in 20 ml water, centrifuged at 500 rpm for 10 minutes, the pellet is discarded and the supernatant recovered and diluted it 1:1 with water.

Unsprouted cloves of similar weights (±0.5 g) from 6 bulbs of each garlic were sampled and homogenized in 10 volumes of water using a high-speed tissue homogenizer (Sorval omnimixer, Newton, Conn.) for one minute. The crude homogenates were incubated at room temperature for 30 minutes to allow enzymatic lysis of the flavor precursors, centrifuged and the supernatants were filtered through a 0.2 µm pore-size cellulose-acetate filter (Alltech Associates, Inc., Deerfield, Ill.). The homogenates were stored at −20° C. until thiosulfinates, pyruvate and soluble solids analysis were done. Similar methods were used to prepare bulbil homogenates.

To determine the amount of allicin present, an alliin (Sigma, St. Louis, Mo.) stock solution is prepared. The sample can be used to generate a calibration curve. For example, a stock of 2.5 mM alliin can be prepared (0.443 mg/ml). The preparation of allicin standards are according to Table 4.

TABLE 4

| Allicin standards | | | | | | |
|---|---|---|---|---|---|---|
|  | Std 0 | Std 100 | Std 200 | Std 400 | Std 600 | Std 800 |
| garlic juice (µl) | 500 | 500 | 500 | 500 | 500 | 500 |
| water (µl) | 4500 | 4400 | 4300 | 4100 | 3900 | 3700 |
| Alliin (0.443 mg/ml) (µl) | 0 | 100 | 200 | 400 | 600 | 800 |
| Final Vol. (µl) | 5000 | 5000 | 5000 | 5000 | 5000 | 5000 |
| Dilution |  | 50 | 25 | 12.5 | 8.3333333 | 6.25 |
| Final [alliin] (mg/ml) | 0 (basal) | 0.00886 | 0.01772 | 0.03544 | 0.05316 | 0.07088 |
| Allicin conc (alliin × 0.458) | 0 (basal) | 0.004058 | 0.008116 | 0.016232 | 0.024347 | 0.03246304 |

Thiosulfinates were quantified by HPLC following the general conditions described by Block et al. (*J. Agric. Food Chem.* 40:2418-30, 1992). In brief, normal phase (Si) chromatography on a 250 mm×4.6 mm, Microsorb 5 µm Silica column (Rainin Instrument Co Inc., Woburn, Mass.) with a Whatman HC Pellosil guard column (15 mm×4.6 mm) involved isocratic elution with 10% 2-propanol/90% hexane (v/v) solvent delivered with a Water 510 pump at a flow rate of 1.8 ml/min. The column was at ambient temperature.

Solvent A: 100% Methanol (For cleaning only); Solvent B: 90% Hexane+10% Isopropanol. Sample injection volume was 25 µL with a Waters 712 WISP and run time was 10 minutes. Peak detection utilized a Waters 996 Photodiodide Array Detector with a wavelength range of 190 to 600 nm, extracted channels at 210 and 254 nm. Peak area was measured using the software Waters Empower Build 1154 with Service Packs A, B. Peak assignment for allicin and the unsymmetrical thiosulfinates Methyl allyl, Allyl methyl, 1-Propenyl allyl and Allyl 1-propenyl was carried out by reference substances, retention times and absorption spectra.

As shown in Table 5, the green garlic plantlets contain the thiosulfinates associated with the pulmonary and other health related benefits. The allicin content is approximately one half to two thirds (50-66%) the levels in clove garlic of the same variety. However, allicin and its beneficial properties are destroyed by heat during cooking. Therefore, although the concentration of allicin in green garlic is about one half the concentration in clove garlic, green garlic can be consumed fresh and therefore provides for effective delivery of these compounds. Because the green garlic food product can be consumed fresh, the health related properties of thiosulfinates are not lost during cooking. The AllS(O)Spropenyl data may not reflect the actual content since in some cases this peak partially overlaps with the allicin peak, and only the most abundant isomer was considered (the peak for the other isomer can be difficult to distinguish).

Due to the large amount of allicin observed in bulbils, the bulbils were re-extracted and re-analyzed, as shown in Table 6.

TABLE 5

Allicin Content of *Allium sativum* 'dophioscorodon' cv. Music

HLPC Traces showing Area Under the Curve

|  | Allicin | AllS(O)SMe | AllS(O)SMe | AllS(O)SMe | AllS(O)SPropenyl |
| --- | --- | --- | --- | --- | --- |
| std 0 | 641686 | 10969 | 26135 | 37104 | 16112 |
| std 50 | 770262 | 6921 | 6678 | 13599 | 31866 |
| std 100 | 842280 | 6437 | 6068 | 12505 | 24621 |
| std 200 | 1098252 | 7093 | 6381 | 13474 | 26041 |
| Clove 1 | 6206433 | 141320 | 181405 | 322725 | 360904 |
| Clove 2 | 5685254 | 158816 | 212617 | 371433 | 282733 |
| Leaves 1 | 3658857 | 446881 | 936804 | 1383685 | 738512 |
| Leaves 2 | 2966906 | 506955 | 1153503 | 1660458 | 569216 |
| Bulbils 1 | 20530121 | 951528 | 1284567 | 2236095 | 1245912 |
| Bulbils 2 | 21681151 | 1152914 | 1502243 | 1631236 | 1365535 |
| Bulbs 1 | 2131649 | 131405 | 223499 | 354904 | 322116 |
| Bulbs 2 | 2302502 | 128993 | 204264 | 333257 | 265237 |
| Bulbs 3 | 1345384 | 94690 | 165846 | 260536 | 212038 |
| Pseudo Stalk 1 | 3134085 | 527845 | 831595 | 1359440 | 602545 |
| Pseudo Stalk 2 | 3076921 | 563382 | 847546 | 1410928 | 581606 |
| Roots 1 | 1592696 | 104578 | 286901 | 391479 | 476717 |
| Roots 2 | 1749521 | 114744 | 292258 | 407002 | 488051 |

TABLE 6

Re-extraction and re-runs of bulbils tissues for Music variety

Area under the curve

|  | Allicin | AllS(O)SMe | AllS(O)SMe | AllS(O)SMe | AllS(O)SPropenyl |
| --- | --- | --- | --- | --- | --- |
| std 0 | 617027 |  |  |  |  |
| std 50 | 750237 |  |  |  |  |
| std 100 | 843352 |  |  |  |  |
| std 200 | 1114448 |  |  |  |  |
| std 400 | 1481978 |  |  |  |  |
| Bulbils 3 | 20559903 | 85832 | 1270335 | 1356167 | 1325601 |
| Bulbils 4 | 21989520 | 946488 | 1446633 | 2393121 | 1397453 |
| Bulbils 5 | 20809032 | 848793 | 1289228 | 2138021 | 1172645 |
| Bulbils 6 | 19715780 | 815378 | 1224021 | 2039399 | 1202569 |

Example 8

Food Products

This example describes food products that were prepared containing the green garlic of the present disclosure. One skilled in the art will recognize that similar methods can be used to prepare any food product where garlic flavor is desired.

Fresh green garlic tempura with chipotle sauce, pan-seared green garlic wrapped fresh diver scallops with a lemon butter sauce, a puree of potato and green garlic soup, and, spicy stir fried shrimp with green garlic and ginger were prepared by a professional chef. Patrons raved.

Example 9

In Vitro Assays for Therapeutic Uses of Green Garlic

This example describes in vitro assays that can be used to determine the beneficial effects of green garlic (or extracts thereof). One skilled in the art will recognize that other assays can be used.

The method of Briggs et al. (*J. Nutr.* 131:2619-22, 2001, herein incorporated by reference) can be used to determine the effect of green garlic extracts on platelet aggregation. Blood is drawn by venipuncture from a mammal, such as a human or laboratory animal, for example through a 21-gauge butterfly needle. Nine volumes of blood are mixed with 1 volume of 38 g/L sodium citrate. The blood is then mixed with an equal volume of 9 g/L buffered saline.

Garlic juice (see Example 10) can be tested for platelet inhibition at different concentrations (such as 1, 10 and 100 mL juice/L blood) after different incubation times in the blood (such as 4 and 30 min). Platelet aggregation is induced by collagen (2 mg/L). Results can be expressed as the percentage of platelet aggregation inhibited by green garlic juice. This is calculated using the ratio of the incubation results to a parallel control to which an equivalent volume of saline had been added in place of green garlic juice. Platelet aggregation is measured as described in Example 10.

It is expected that platelet aggregation will decrease in the presence of green garlic juice or extract compared to an amount of aggregation in the control sample.

Example 10

Therapeutic Properties of Green Garlic in a Mammal

This example describes methods that can be used to administer the green garlic of the present application to a mammal, for example to increase an amount of a sulfur-containing compound, such as one or more thiosulfinates, in a mammal. Such methods can be used to treat (such as prevent) cardiovascular diseases, such as myocardial infarction, stroke and multiple arteriosclerosis, as well as cancer.

Decrease Platelet Aggregation

In one example, green garlic is administered to a mammal, thereby decreasing platelet aggregation in the mammal. The method of Briggs et al. (*J. Nutr.* 131:2619-22, 2001, herein incorporated by reference) can be used to determine the effects in a laboratory mammal. Briefly, a laboratory mammal, such as a dog, is prepared with mechanically damaged and stenosed coronary arteries. Briefly, dogs are anesthetized, the left chest entered and the heart exposed. An electromagnetic flow probe is placed on the circumflex coronary artery. Distal to the probe, the artery was clamped to produce intimal and medial damage and narrowed (60-70% diameter reduction) by placing a plastic cylinder around the outside of the vessel. A thrombus will form in the narrowed lumen, causing a slow (6-7 mm) decline in measured coronary blood flow. When flow reaches zero, the cylinder is gently shaken and the thrombus embolized distally, restoring coronary blood flow. This periodic thrombus formation followed by embolization produces cyclic flow reductions (CFR). The rate of flow decline in this model is directly related to the rate of accumulation of platelets in the narrowed lumen. Thus, the frequency of CFR is a direct measurement of in vivo platelet activity.

A green garlic extract is prepared and administered to the mammal. For example, 10 green garlic plants can be chopped and juiced with a commercial juicer. The green garlic juice is incubated under conditions that permit activation of alliinase (such as 22° C. for 30 minutes). The juice is centrifuged to remove pulp (such as twice at 4000×g for 10 minutes). The resulting supernatant is saved (can be stored at −20° C. until use).

After establishment of CFR, dogs are administered an IV dose of 0.09 ix 0.01 mL/kg green garlic juice via a catheter inserted into the femoral vein. Both before CFR and 20 mm after administration of juice, blood (10-20 ml) is drawn through a catheter inserted into the femoral artery to a syringe containing 2 ml of 38 g/L sodium citrate. The blood is mixed with an equal volume of 9 g/L saline. Ex vivo platelet aggregation is assessed using these samples and a whole-blood electrical impedance aggregometer (such as from Chronolog, Havertown, Pa.). For each measurement, two electrodes are inserted into a tube containing the blood mixture. When a platelet agonist was added, platelets aggregate to the electrodes, causing an increase in electrical impedance. Collagen (1 and 2 mg/L), collagen (0.125 mg/L) with epinephrine (1.0 mg/L), ADP (20 µmol/L) with and without epinephrine (1.0 mg/L), and phorbol myristate acetate (PMA, 0.5 µmol/L) can be used as agonists. Two hours after administration of green garlic juice, damage to the stenosed region of the coronary artery can be repeated to determine whether CFR would return.

In another example, the green garlic is administered orally to the mammal. In one example, the green garlic is consumed by the mammal orally. In another example, a homogenate of the green garlic is prepared one hour before initiating CFR (for example by homogenizing the green garlic in deionized water). The homogenate is incubated under conditions that permit activation of alliinase (such as 22° C. for 30 minutes). The juice is centrifuged to remove pulp (such as twice at 4000×g for 10 minutes). The resulting supernatant is saved (can be stored at −20° C. until use). The pH was then adjusted to 3.0 (the approximate acidity of the dog stomach) with HCl and the mixture was stored at 4° C. until it is used <1.5 h later. CFR is initiated. Before dissecting out the coronary artery, dogs are fitted with a gastric tube with the tip placed into the duodenum immediately distal to the gastrointestinal sphincter. Green garlic homogenate (2 g green garlic/kg) is mixed with 9 g/L saline to a total volume of 50 mL and then administered through the tube gradually over 5 min. Blood is drawn shortly before and 2.5-3 h after administration of green garlic homogenate to measure changes in ex vivo platelet aggregation as described above. Approximately one h after abolishment of CFR, additional damage was made to the stenosed portion of the vessel and 0.2 µg/(kg·min) epinephrine is infused for 20 min to attempt to renew CFR.

It is expected that intravenous (iv) or intragastric administration of green garlic extract will reduce platelet aggregation as evidenced by decreased cyclic flow reductions.

Decrease Plasma Homocysteine

In another example, green garlic is administered to a mammal, thereby decreasing plasma homocysteine levels in the mammal. The method of described in U.S. Pat. No. 6,129,918 can be used (herein incorporated by reference). Briefly, green garlic and extracts can be administered (such as orally or via iv) to the subject. Green garlic can be extracted in water, alcohol (such as anhydrous or hydrous alcohol), or mixtures thereof. The extract can be prepared at room temperature, for example for between three months and two years. If needed, the green garlic plants can be crushed and homogenized to produce the plant juice. Oxidized iron can be added to the juice. The thus prepared extract may be used as is, concentrated into a concentrate, or in powdered form after concentration under vacuum or liophilization.

Growing male rats of Sprague-Dawley strain (120-180 grams) are fed an amino acid defined diet containing succinylsulfathiozole (10 g/kg diet), but no folk acid, or the same diet supplemented with 4% by weight of garlic in the form of the green garlic extract as described above, or diet/vitamin $B_6$ (8 mg/kg diet) or vitamin $B_{12}$ (50 µg/kg diet) or folic acid (5 mg/kg diet), or the extract and the vitamins and the folic acid in the amounts specified.

The animals are fed ad labium and have access to water at all times. The feeding continues for four weeks. At the conclusion of the feeding, the rats are fasted overnight and blood drawn from the inferior vena cava under anesthetic conditions. Blood samples are kept on ice and centrifuged at 200×g for five minutes at 4° C. within one hour of collection. Plasma is collected and stored at −80° C. until analysis. Plasma concentration of total homocysteine can be determined by the HPLC-fluorescence method of Vester and Rasmussen (*Eur. J. Clin. Chem. Clin. Biochem.* 29:549-54, 1991, herein incorporated by reference).

It is expected that the green garlic extract will reduce plasma homocysteine concentration in the experimental animals than the control animals not receiving the garlic extract.

Administration to Humans

One skilled in the art will appreciate that similar methods can be used to administer green garlic or an extract thereof to a human or other mammalian subject, such as a subject in need of decreased plasma homocysteine levels or decreased platelet aggregation. For example, green garlic can be fed to a human orally. In another example, a green garlic extract or homogenate is prepared and administered to the subject, for example orally or intravenously.

The dosage level of green garlic may vary according to age, body weight and body condition of the human recipient. Dosage levels based on body weight can be calculated from the relative amounts used in the animal tests described. In particular examples, oral administration of at least 1 mg of green garlic (or an extract thereof) per day for adults is used, such as at least 3.5 mg of green garlic daily, such as 3.5-25 mg daily. In another example, at least 0.1 µg of one or more thiosulfinates are administered daily, such as at least 0.1-50 µg of one or more thiosulfinates, for example at least 0.1 µg of allicin daily, at least 0.1 µg S-methyl cysteine sulphoxide daily, at least 0.1 µg trans S-1-propenyl cysteine sulphoxide daily, at least 0.1 µg S-propyl cysteine sulphoxide daily, or combinations thereof.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A green garlic produced by a method, comprising:
   growing a hardneck garlic bulbil; and
   harvesting a plantlet from the bulbil, thereby producing green garlic, wherein the green garlic comprises at least 0.1 milligram of thiosulfinates per gram of green garlic, and wherein the thiosulfinates comprise thio-2-propene-1-sulfinic acid S-allyl ester (allicin) S-allyl cysteine sulphoxide (alliin), S-methyl cysteine sulphoxide (methiin), trans S-1-propenyl cysteine sulphoxide (isoalliin), S-propyl cysteine sulphoxide (propiin), or combinations thereof.

2. The green garlic of claim 1, wherein the method further comprises planting the hardneck garlic bulbil under conditions that result in germination of the bulbil prior to growing the bulbil.

3. The green garlic of claim 1, wherein harvesting comprises removing the bulbil from a growth media.

4. The green garlic of claim 1, wherein the hardneck garlic bulbil was exposed to conditions that terminated dormancy of the bulbil, prior to growing the bulbil.

5. The green garlic of claim 4, wherein the conditions that terminated dormancy of the bulbil comprise exposure to a temperature of 4° C. for at least 20 days.

6. The green garlic of claim 1, wherein the bulbil is grown indoors.

7. The green garlic of claim 1, wherein the bulbil is grown in quantities sufficient for commercial production.

8. The green garlic of claim 7, wherein commercial production of exceeds 100 pounds of green garlic annually.

9. The green garlic of claim 2, wherein at least 0.1 acres of bulbils are planted.

10. The green garlic of claim 2, wherein the bulbils are planted at a density of 1-7 million bulbils per acre.

11. The green garlic of claim 1, wherein the bulbil is an *Allium sativum* L. bulbil.

12. The green garlic of claim 11, wherein the bulbil is an *Allium sativum* variety 'ophioscorodon' subvariety Music bulbil; *Allium sativum* variety 'ophioscorodon' subvariety Red Rezan bulbil; *Allium sativum* variety 'ophioscorodon' subvariety Georgia Crystal bulbil; *Allium sativum* variety 'ophioscorodon' subvariety German Red bulbil; or *Allium sativum* variety 'ophioscorodon' subvariety Roja bulbil.

13. The green garlic of claim 2, wherein the green garlic is harvested from the bulbil at least 30 days after planting the bulbil.

14. A food product comprising the green garlic of claim 1.

15. A crop comprising the green garlic of claim 1.

16. A neutricutical comprising the green garlic of claim 1, or an extract thereof.

17. The green garlic of claim 1, further comprising packaging the green garlic after harvesting.

18. The green garlic of claim 1, wherein harvesting the plantlet from the bulbil comprises cutting the plantlet from the bulbil.

19. The green garlic of claim 1, wherein the bulbils are less than 3 mm in length.

20. The green garlic of claim 1, wherein the bulbils are 3-8.9 mm in length.

21. The green garlic of claim 1, wherein the bulbils are at least 9 mm in length.

22. A package or container comprising the green garlic of claim 1.

23. The package or container of claim 22, wherein the green garlic is of substantially a uniform size.

24. The green garlic of claim 1, wherein the method comprises growing the hardneck garlic bulbil for 30-45 days.

25. The green garlic of claim 1, wherein the method comprises growing the hardneck garlic bulbil for at least 30 days.

26. A green garlic produced by a method, comprising:
    growing a hardneck garlic bulbil for 30-45 days; and
    harvesting a plantlet from the bulbil, thereby producing green garlic, wherein the green garlic comprises at least 0.1 milligram of thiosulfinates per gram of green garlic.

27. A food product comprising the green garlic of claim 26.

* * * * *